United States Patent [19]
Hofmann

[11] Patent Number: 6,009,347
[45] Date of Patent: Dec. 28, 1999

[54] ELECTROPORATION APPARATUS WITH CONNECTIVE ELECTRODE TEMPLATE

[75] Inventor: Günter A. Hofmann, San Diego, Calif.

[73] Assignee: Genetronics, Inc., San Diego, Calif.

[21] Appl. No.: 09/014,291

[22] Filed: Jan. 27, 1998

[51] Int. Cl.⁶ ................................................ A61N 1/30
[52] U.S. Cl. ........................... 604/21; 604/20; 607/116; 607/143; 607/148
[58] Field of Search ................ 604/21, 20; 607/148, 607/108, 143, 116; 435/173.6

[56] References Cited

U.S. PATENT DOCUMENTS

| | | |
|---|---|---|
| 1,099,062 | 6/1914 | Laposkey . |
| 5,318,814 | 6/1994 | Hofmann ................................. 604/20 |
| 5,344,440 | 9/1994 | Stephen . |
| 5,439,440 | 8/1995 | Hofmann ................................. 604/20 |
| 5,674,267 | 10/1997 | Mir et al. . |
| 5,873,849 | 2/1999 | Bernard . |

FOREIGN PATENT DOCUMENTS

WO 96 39226  12/1996  WIPO .............................. A51N 1/32

*Primary Examiner*—Mark Bockelman
*Attorney, Agent, or Firm*—Baker & Maxham

[57] ABSTRACT

An electrode template apparatus, comprises a three dimensional support member having opposite surfaces, a plurality of bores extending through the support member and through the opposite surfaces, a plurality of conductors on the member separately connected to the plurality of bores, a plurality of electrodes selectively insertable in the plurality of bores so that each electrode is connected to at least one conductor for connecting the electrodes to a power supply.

23 Claims, 13 Drawing Sheets

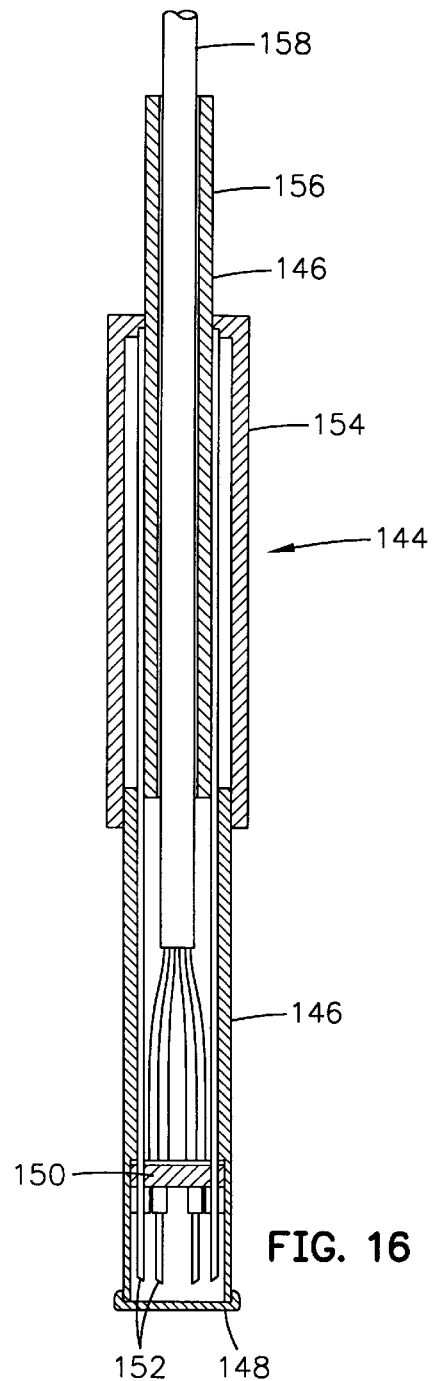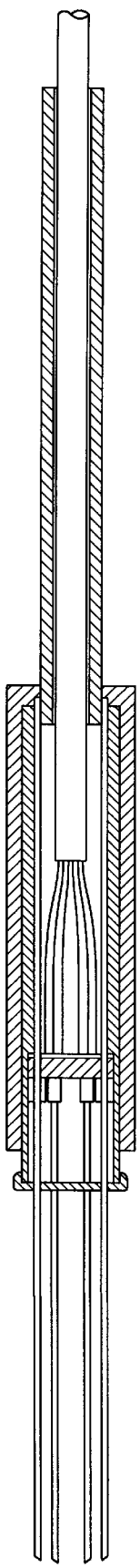
FIG. 16
FIG. 17

ELECTROPORATION APPARATUS WITH CONNECTIVE ELECTRODE TEMPLATE

BACKGROUND OF THE INVENTION

The present invention relates to electroporation and pertains particularly to an apparatus with connective electrode template for electroporation therapy.

The present invention relates to the treatment of ailments in humans and other mammals, and more particularly, to an improved method and apparatus for the application of controlled electric fields for in vivo delivery of genes and pharmaceutical compounds into live cells of a patient by electroporation.

A cell has a natural resistance to the passage of molecules through its membranes into the cell cytoplasm. Scientists in the 1970's first discovered "electroporation", where electrical fields are used to create pores in cells without causing permanent damage to them. This discovery made possible the insertion of large molecules directly into cell cytoplasm. Electroporation was further developed to aid in the insertion of various molecules into cell cytoplasm by temporarily creating pores in the cells through which the molecules pass into the cell.

Electroporation has been used to implant materials into many different types of cells. Such cells, for example, include eggs, platelets, human cells, red blood cells, mammalian cells, plant protoplasts, plant pollen, liposomes, bacteria, fungi, yeast, and sperm. Furthermore, electroporation has been used to implant a variety of different materials, referred to herein as "implant materials", "implant molecules", "implant agents". These materials have included DNA, genes, and various chemical agents.

Electroporation has been used in both in vitro and in vivo procedures to introduce foreign material into living cells. With in vitro applications, a sample of live cells is first mixed with the implant agent and placed between electrodes such as parallel plates. Then, the electrodes apply an electrical field to the cell/implant mixture.

With in vivo applications of electroporation, electrodes are provided in various configurations such as, for example, a caliper that grips the epidermis overlying a region of cells to be treated. Alternatively, needle-shaped electrodes may be inserted into the patient, to access more deeply located cells. In either case, after the implant agent is injected into the treatment region, the electrodes apply an electrical field to the region. Examples of systems that perform in vivo electroporation include the Electro Cell Manipulator ECM 600 product, and the Electro Square Porator T820, both made by and available from the BTX Division of Genetronics, Inc.

Electroporation has been recently suggested as an alternate approach to the treatment of certain diseases such as cancer by introducing a chemotherapy drug directly into the cell. For example, in the treatment of certain types of cancer with chemotherapy it is necessary to use a high enough dose of a drug to kill the cancer cells without killing an unacceptable high number of normal cells. If the chemotherapy drug could be inserted directly inside the cancer cells, this objective could be achieved. Some of the best anti-cancer drugs, for example, bleomycin, normally cannot penetrate the membranes of certain cancer cells effectively. However, electroporation makes it possible to insert the bleomycin into the cells.

A number of experiments have been conducted to test therapeutic application of electroporation for cancer treatment in a process now termed electrochemotherapy. This treatment is carried out by infusing an anticancer drug directly into the tumor and applying an electric field to the tumor between a pair of electrodes. The field strength must be adjusted reasonably accurately so that electroporation of the cells of the tumor occurs without damage to any normal or healthy cells. This can normally be easily carried out with external tumors by applying the electrodes to opposite sides of the tumor so that the electric field is between the electrodes. The distance between the electrodes can then be measured and a suitable voltage according to the formula $E=V/d$ can then be applied to the electrodes. It would be desirable to have an electrode apparatus having electrodes that can be inserted into or adjacent to tumors so that predetermined electric fields can be generated in the tumor tissue for electroporation of the cells of the tumor.

One type of in vivo electroporation application presently under active research under the direction of the applicant is electro-chemotherapy, which uses electroporation to deliver chemotherapeutic agents directly into tumor cells. This treatment is carried out by infusing an anticancer drug directly into the tumor and applying an electric field to the tumor between a pair of electrodes. The molecules of the drug are suspended in the interstitial fluid between and in and around the tumor cells. By electroporating the tumor cells, molecules of the drug adjacent to many of the cells are forced or drawn into the cell, subsequently killing the cancerous tumor cell.

Electroporation in this application is especially beneficial because electroporation can help minimize the amount of implant agent used, these chemicals frequently being harmful to normal cells. In particular, less of the implant agent can be introduced into the tumorous area because the electroporation will enable more of the implant agent to actually enter the cell. Electroporation is also beneficial for chemotherapy because some of the most promising anti-cancer drugs, such as Bleomycin, normally cannot penetrate the membranes of certain cancer cells effectively. However, recent experiments with electroporation demonstrated that it is possible to insert the Bleomycin directly into the cells.

Known electroporation techniques (both in vitro and in vivo) function by applying a brief high voltage pulse to electrodes positioned around the treatment region. The electric field generated between the electrodes causes the cell membranes to temporarily become porous, whereupon molecules of the implant agent enter the cells. In known electroporation applications, this electric field comprises a single square wave pulse on the order of 1000 V/cm, of about 100 $\mu$s duration. Such a pulse may be generated, for example, in known applications of the Electro Square Porator T820, made by the BTX Division of Genetronics, Inc.

Although known methods of electroporation may be suitable for certain applications, the electric field may actually damage the electroporated cells in some cases. For example, an excessive electric field may damage the cells by creating permanent pores in the cell walls. In extreme cases, the electric field may completely destroy the cell.

SUMMARY OF THE INVENTION

In accordance with a primary aspect of the present invention an electrode template apparatus, comprises a three dimensional support member having opposite surfaces, a plurality of bores extending through said support member, a plurality of conductors on said member separately connected to contacts in said plurality of bores, a plurality of electrodes selectively insertable in said plurality of bores so that each conductor is connected to at least one electrode, and means for connecting said electrode template to a power supply.

BRIEF DESCRIPTION OF THE DRAWING

The above and other objects and advantages of the present invention will become apparent from the following description when read in conjunction with the accompanying drawings, wherein:

FIG. 16 is a side elevation view illustrating another embodiment of the invention showing the needle electrodes mounted in a holder with the electrodes in the retracted position;

FIG. 17 is a view like FIG. 16 showing the needle electrodes in the extended position;

DETAILED DESCRIPTION OF THE PREFERRED EMBODIMENTS

Figure 1:
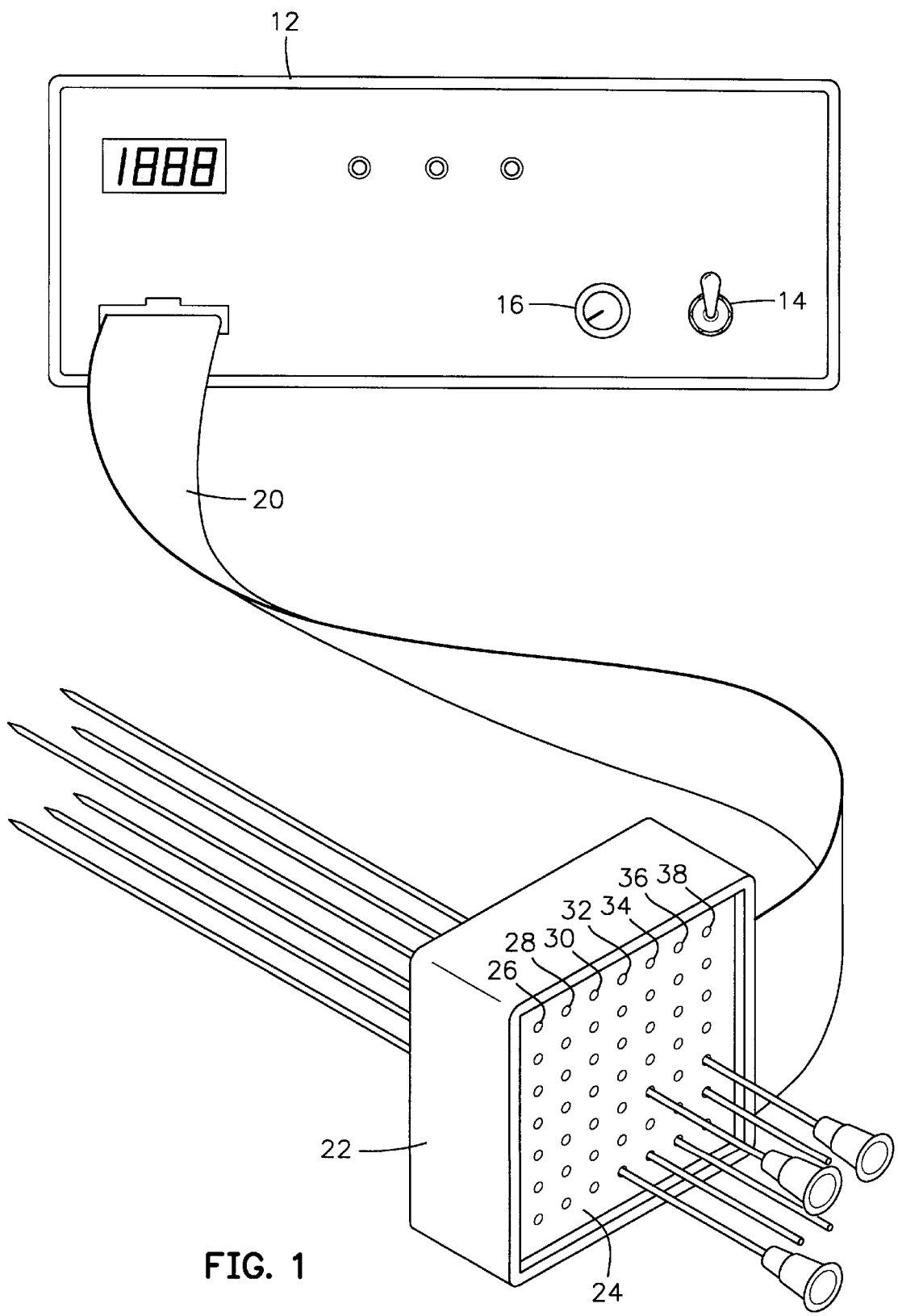
FIG. 1 is a perspective view illustrating a system employing an exemplary embodiment of the present invention.

Referring to FIG. 1 of the drawing, an electroporation system embodying an exemplary embodiment of the present invention is illustrated and designated generally by the numeral 10. The system comprises a pulse generator 12 for generating high voltage pulses and is preferably of the type sold under the mark "Medpulser III" by Genetronics, Inc. The pulse generator is preferably of the type disclosed in application Ser. No. 08/905,240, entitled "Method of Treatment Using Electroporation Mediated Delivery of Drugs and Genes", filed Aug. 1, 1997, wherein a user defined pulse may be selected and various parameters programmed in. This enables pre-selectable pulsing schemes suitable for the particular applications.

The pulsing unit has the usual control panel with a power selector switch 14 and may also have other controls such as a remote activation means 16. The panel would also have various indicators to indicate to the operator various conditions and parameters, such as a digital readout 18 for therapy set-point. A conductor cable 20 connects the pulse generator to a connector and template 22 for a plurality of electrodes. The electrode connector and template 22 serves to connect selected electrodes to selected conductors, which in turn connect the electrodes to the pulse generator. The template also aids in establishing a pre-determined array or multiple arrays of electrodes A precise and controlled voltage must be applied to the tissue in order to provide the optimum electroporation or poration of the cells without damage to the cells. Therefore, it is essential that the spacing of the electrodes be known so that the optimum voltage may be applied between the selected electrodes. The voltage must be applied in accordance with the spacing between the electrodes in order to apply the optimum voltage to the cells. The connector template 22 provides a means of selectively positioning any number of electrodes in a pre-determined array with pre-determined spacing.

The illustrated system was designed for using needle electrodes to apply electroporation therapy to prostate cancer. However, it will be appreciated that this system may be utilized for any number of external and internal tumors or organs of the body that can be reached from a body surface. For example, this system will enable the treatment of prostate tumors, breast tumors, local tumors pancreatic tumors, liver tumors, or any other organ within the body that is accessible by needle electrodes or any other manner including open surgery. While the discussion herein has been primarily for the insertion of drugs into cells within tumors, or the like, it will also be appreciated that it can be used for the insertion of DNA or other genetic materials into cells within an organ in the body for altering or generating a genetic response within an organ in the body, or within cells in that organ.

The applicant has found through experimentation that pulsing between multiple pairs of electrodes in a multiple electrode array, preferably set up in rectangular or square patterns, provides improved results over that of pulsing between a pair of electrodes. Disclosed, for example, in application Ser. No. 08/467,566 entitled "Needle Electrodes for Electroporation Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes.

The connector template of the present invention is designed to provide a system for accurately establishing a pre-selected array of needle electrodes with a pre-determined spacing between the multiple electrodes positioned within a tissue where electroporation is desired. The connector 22 is in the form of a support body having a plurality of rows of bores through which needle electrodes may be inserted and connected via the through holes by conductors to the pulse generator by a cable. In the illustrated embodiment, seven rows of seven bores are provided with the bores and rows spaced an equal distance apart. The spacing between the rows may be selected for the particular application, but an exemplary preferred spacing is on the order of about 0.65 cm. With this arrangement, each needle electrode can be spaced a distance of 0.65 cm from an adjacent electrode.

The electrodes are positioned in the grid in a selected manner to cover the desired areas of the tissue and the connections to the electrodes, such that the needles may be selectively distributed throughout the area of a tumor such that each square within the tumor can be subjected to four rotating pulses 90° between pulses. The switching may be done by electronic means square after square at a high frequency so that the total treatment time is on the order of a few seconds. With such an array, high voltages may be applied to the cells between the electrodes without subjecting other areas of tissue to uncomfortable voltage or current levels.

Figure 2:
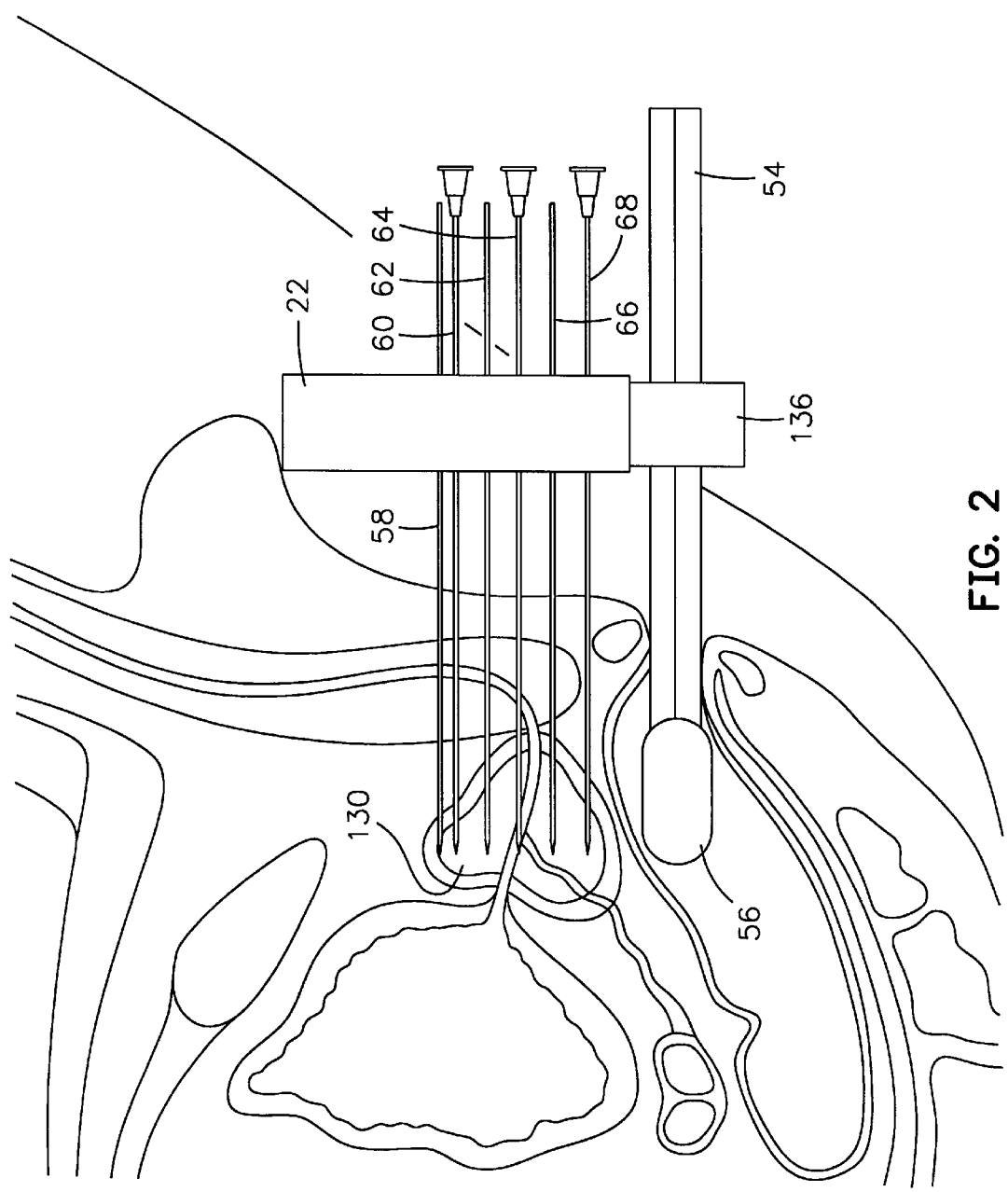
FIG. 2 is a side elevation view showing the embodiment of FIG. 1 in use.

As shown in FIGS. 1 and 2, the connector template is a box-like support structure having a front face 24 and a back face, not shown. A first row of through bores 26, 28, 30, 32, 34, 36, and 38 are connected on the upper surface by means of conductors 40, 42, 44, 46, 48, 50, and 52 to a side edge of the support housing where they are connected by suitable means, either directly or by a plug and socket structure to the cable 20.

Second and subsequent rows of the through holes (not numbered) will be connected by conductors on the different levels of the laminate making up the connector structure as will be subsequently described.

Referring specifically to FIG. 2, the illustrated connector template is shown in use in treatment of a prostate cancer or the like. In this instance, the connector 22 is shown mounted on an elongated support rod 54 of an ultra-sound probe 56 which is shown inserted into the rectum of a patient. The sound probe is used to visualize the prostate and the location of the electrodes in the prostate. The template is then in a position such that a plurality of needle electrodes 58, 60 and 62 in a first row are inserted through three of the horizontal through bores, as illustrated, and into the prostate of the patient. In this instance, two of the needle electrodes, 58 and 62, are illustrated as being solid needle electrodes and a center electrode 60 is shown to be hollow to enable the injection of molecules, such as a drug or therapeutic agent or other material. A second, or lower row of needle electrodes 64, 66 and 68 is directly below the aforementioned electrodes and extend through the through bores of the connector template and into the prostate of the patient. In this instance, two outer needles, 64 and 68, are hollow to enable the injection of a therapeutic or other agent into the prostate of the patient. These may be left in place following the injection of the therapeutic agent and serve as the electrodes for the application of the electrical pulses to the tissue of the prostate or cancer cells within the prostate.

As will be apparent from the aforegoing illustration and description, sufficient needle electrodes may be positioned through the connector template to cover the necessary area of tissue to which electroporation is to be applied. The hollow needles 60, 64 and 68 have outlet ports at the tip, as illustrated. For example, needle 64 is shown to have outlet ports 70 and 72. Similarly, outlet ports in needles 60 and 68 are shown but not given reference numerals.

Figure 3:
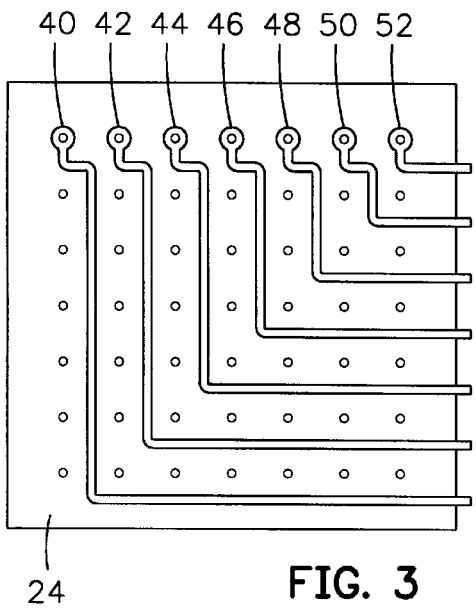
FIG. 3 is a first layer or PC board of the connector of FIG. 1.
Figure 10:
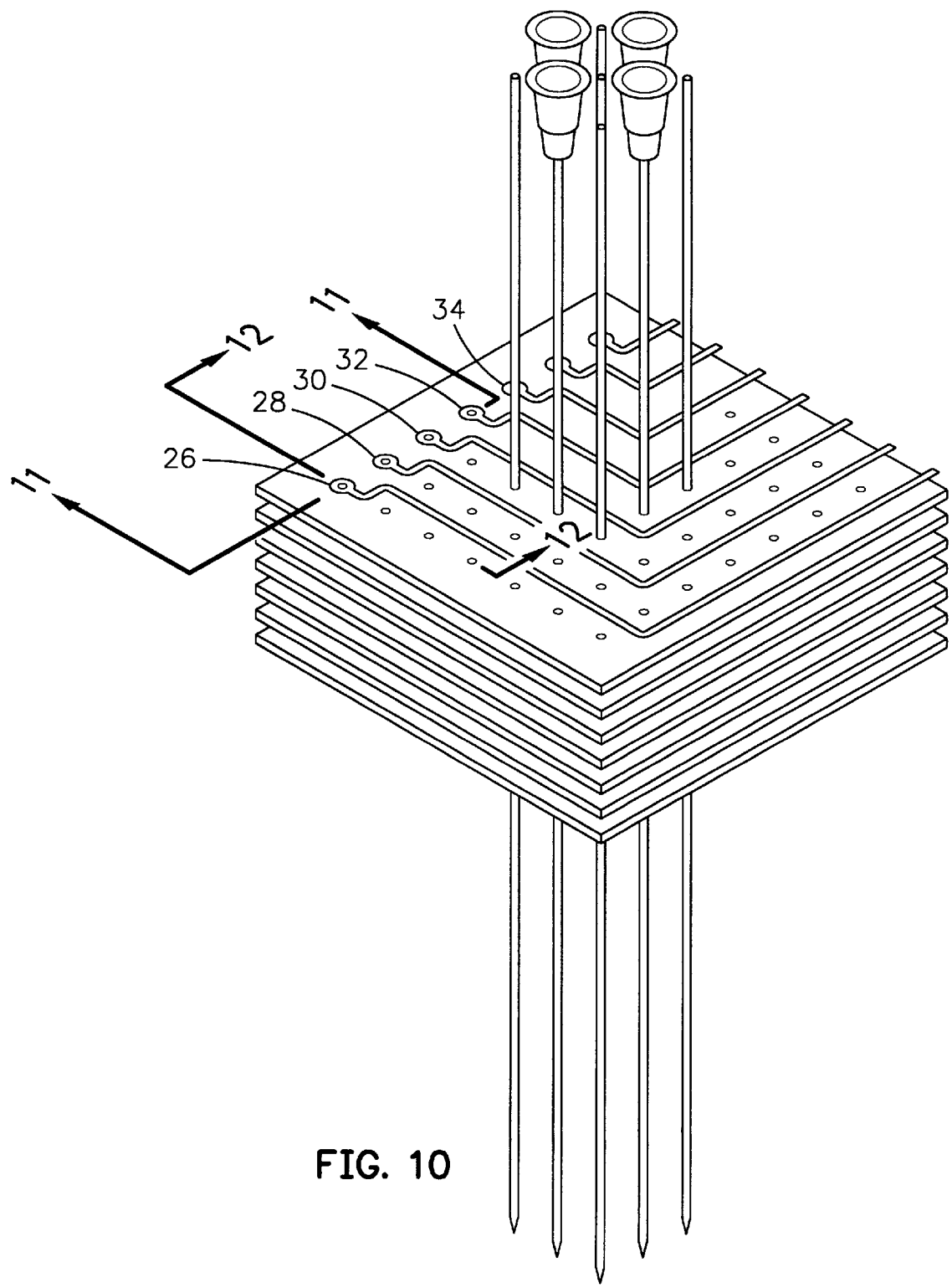
FIG. 10 is a perspective view illustrating the positioning of the layers of FIGS. 3–9 with needles shown in position.

Referring now to FIGS. 3–9, there is illustrated a plurality of printed circuit boards which are stacked together to make up the combined template connector 22. PC board 24, as shown in FIG. 3, forms the face 24 of the connector template unit. This board, as in each of the boards, has a dimension of about 5 cm$^2$. Due to the small space available for the through holes which include the connectors for the respective electrodes, separate circuits for several of the through holes such as each row of the through holes are put on separate PC boards. Thus, as illustrated in FIGS. 3–9, separate connectors and conductors for each of the needle electrodes that will be inserted in a through hole are formed on the surface of a separate PC board. These are then stacked in an array, as illustrated, for example, in FIG. 10. It will be appreciated that the connections for the respective holes in the PC boards can be made in any number of arrangements, such as a vertical or horizontal array.

Figure 4:
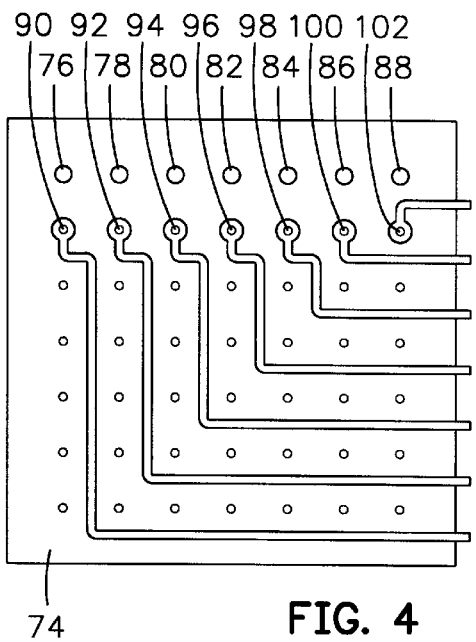
FIG. 4 is a view like FIG. 3 of a second layer of the connector.
Figure 5:
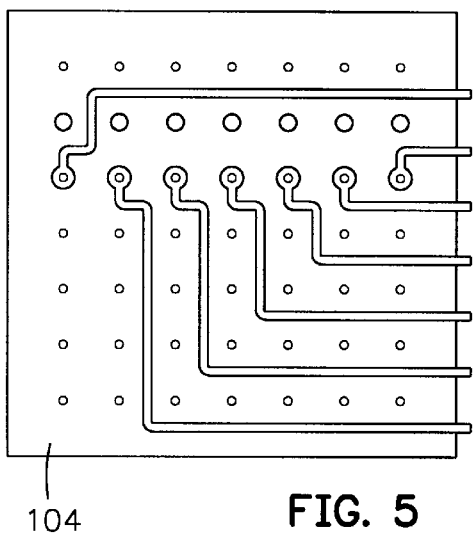
FIG. 5 is a view like FIG. 3 of a third layer of the connector.
Figure 6:
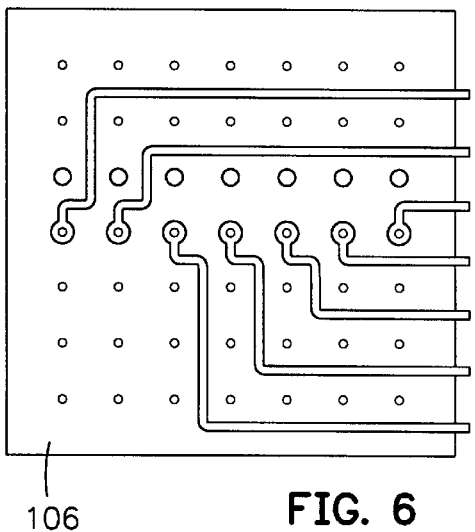
FIG. 6 is a view like FIG. 3 of a fourth layer of the connector.
Figure 7:
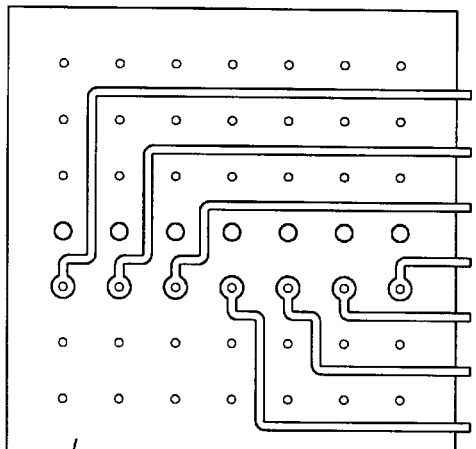
FIG. 7 is a view like FIG. 3 of a fifth layer of the connector.
Figure 8:
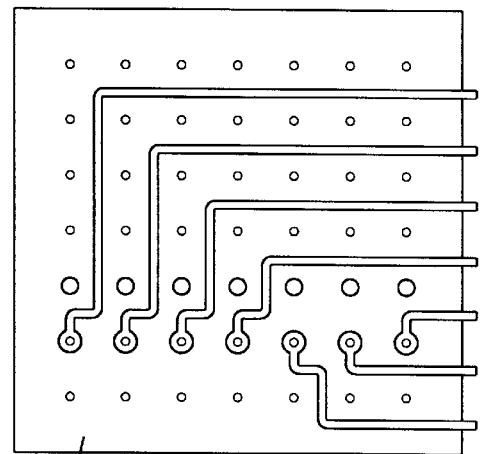
FIG. 8 is a view like FIG. 3 of a sixth layer of the connector.
Figure 9:
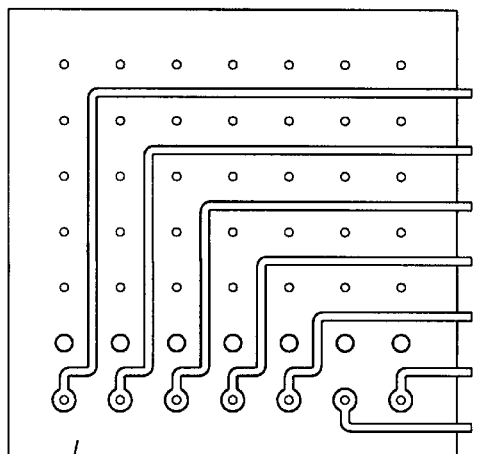
FIG. 9 is a view like FIG. 3 of a seventh layer of the connector.
Figure 11:
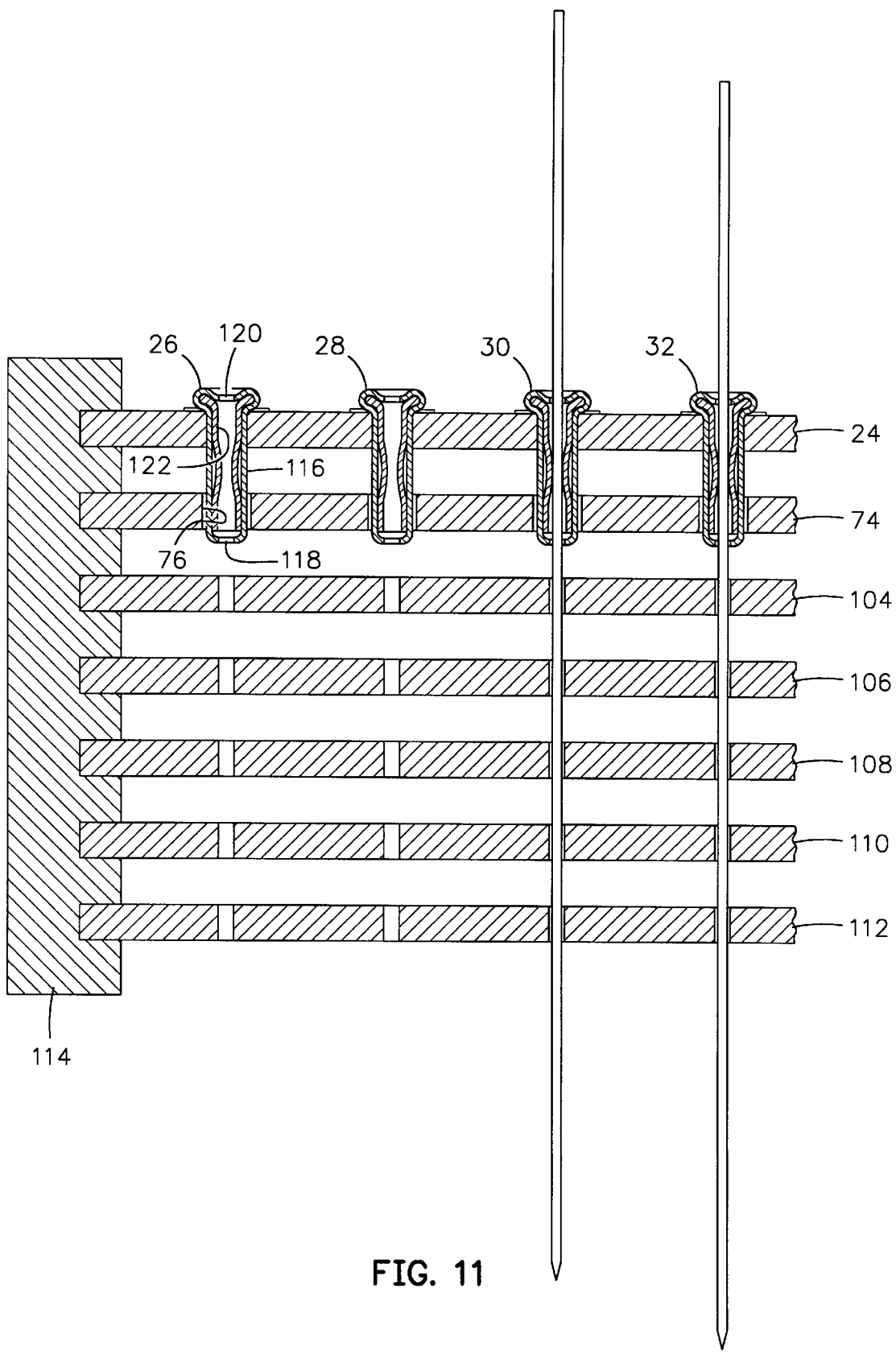
FIG. 11 is a partial sectional view taken along a row of connectors.

Referring now to FIG. 4, it will be seen that a PC board 74, which will be disposed directly below the PC board 24, has a roll of enlarged holes 76–88 which are designed to receive connectors, as illustrated in FIG. 11. In addition, this PC board has a row of connectors 90–102 which forms the second row of connecting holes for the needle electrodes of the assembly. These connecting sockets are connected as in the previous embodiment to conductors extending along the surface of the PC board to an edge of the board where they will be connected to the cable 20.

Referring now to FIG. 11, a sectional view of a portion of the connector assembly is illustrated in section. It shows a plurality of the circuit boards mounted in a frame 114 which supports them in a slightly spaced relationship, as shown. As illustrated, the sockets, such as socket 26, for example, comprises a generally tubular metal shell 116 formed to have an opening 118 at the lower end, and an opening 120 at the upper or inlet end. The shell is formed and crimped around spring contacts 122, which is constricted or bend inward at the center for sliding contact or engagement with a needle. The socket assembly is of a length to extend through bores in the upper PC board 24 through bore 76 in the underlying PC board 74. The socket assemblies are in conductive contact with the printed circuit conductors on the face of the respective board.

Figure 12:
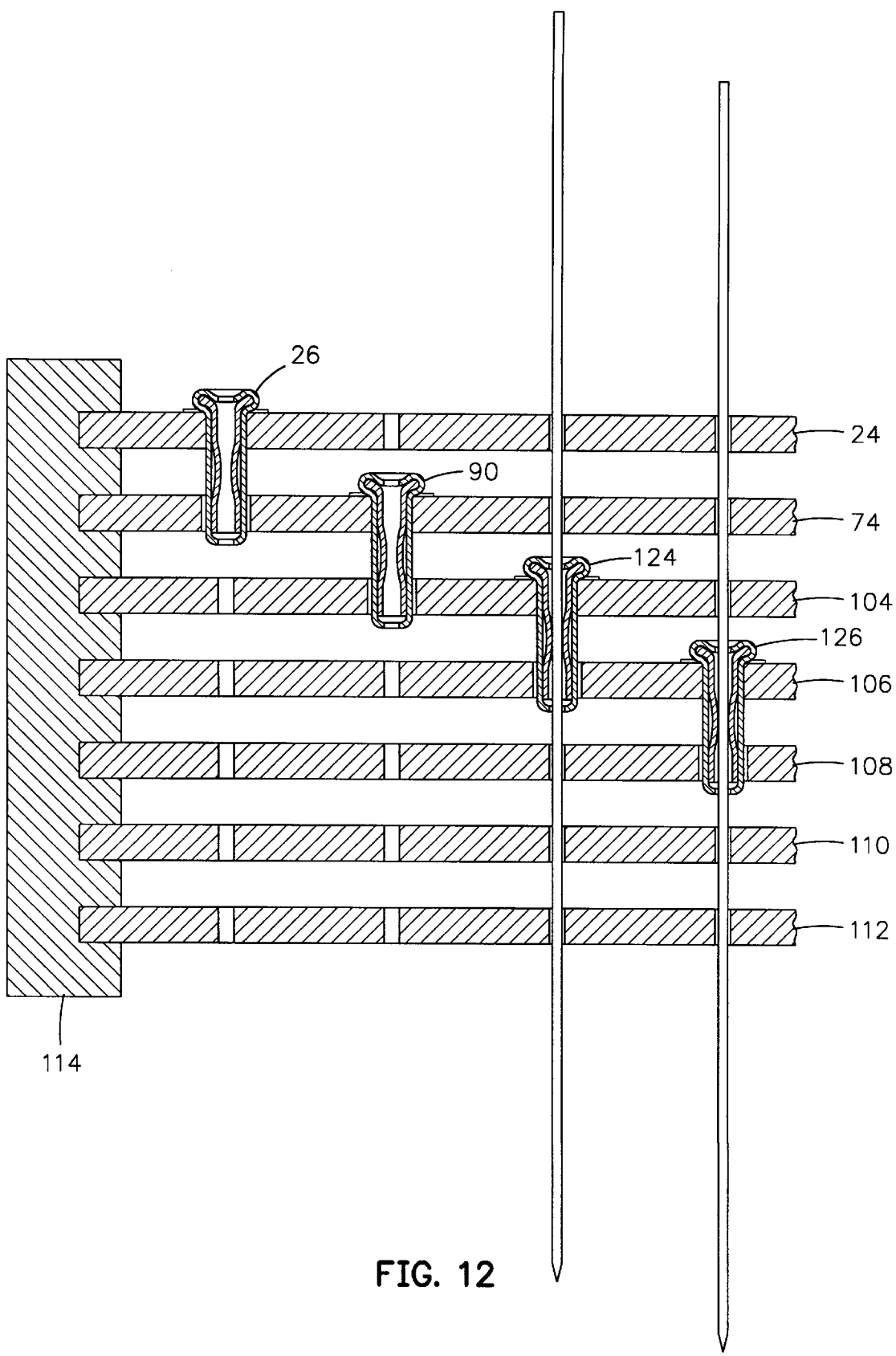
FIG. 12 is a partial sectional view taken across three lines of conductors of the unit.

Referring to FIG. 12, the staggered arrangement of the conductors on the PC boards is illustrated. As illustrated, the second row of conductors or sockets are formed in the PC board 74, which is disposed below the PC board 24. The next lower PC board 104 has a row of conductive sockets, including socket 124 with conductors running along the surface thereof, as previously described. The next row of conductive sockets is on the next lower PC board 106, including a socket 126. Thus, the connectors to the respective electrodes are disposed on different layers within the array of circuit boards. This enables the formation of a combined connector template having very close spacing between the respective conductors, and thereby enable the provision of a high density array, as illustrated.

The above described apparatus of the present invention is shown in use as a prostrate cancer electroporation therapy system in FIG. 2 in the illustration. The template is positioned with the plurality of needles inserted into a prostrate 130, as illustrated. In exemplary embodiment the template is mounted on a handle or extension 132 of an ultra-sound probe 134 by means of a clamp 136. The ultra-sound probe is inserted into the rectum of the patient and utilized by the physician to visualize the tumor in the prostrate. The physician inserts the ultra-sound probe and then inserts the needles into the tumor through the template. Thereafter, chemicals are delivered through a plurality of the needles which are hollow into the tumor in the prostrate. Thereafter, electrical pulses are delivered to the needles, preferably such as in a switching scheme, such as described in the above previously discussed application. For example, at least one pulse is initiated between two opposing pairs of needles, the pulse is then reversed in polarity, then with 90° change of the needle connection, two more pulses are applied.

The above described template array can involve 49 needles, each with a separate connection to the pulse generator. It is desirable in some instances to minimize the number of needles which need to be switched or addressed by the generator. An alternate embodiment hereinafter described involves the arrangement of the needles in parallel connection so that several zones can be switched simultaneously.

Figure 13:
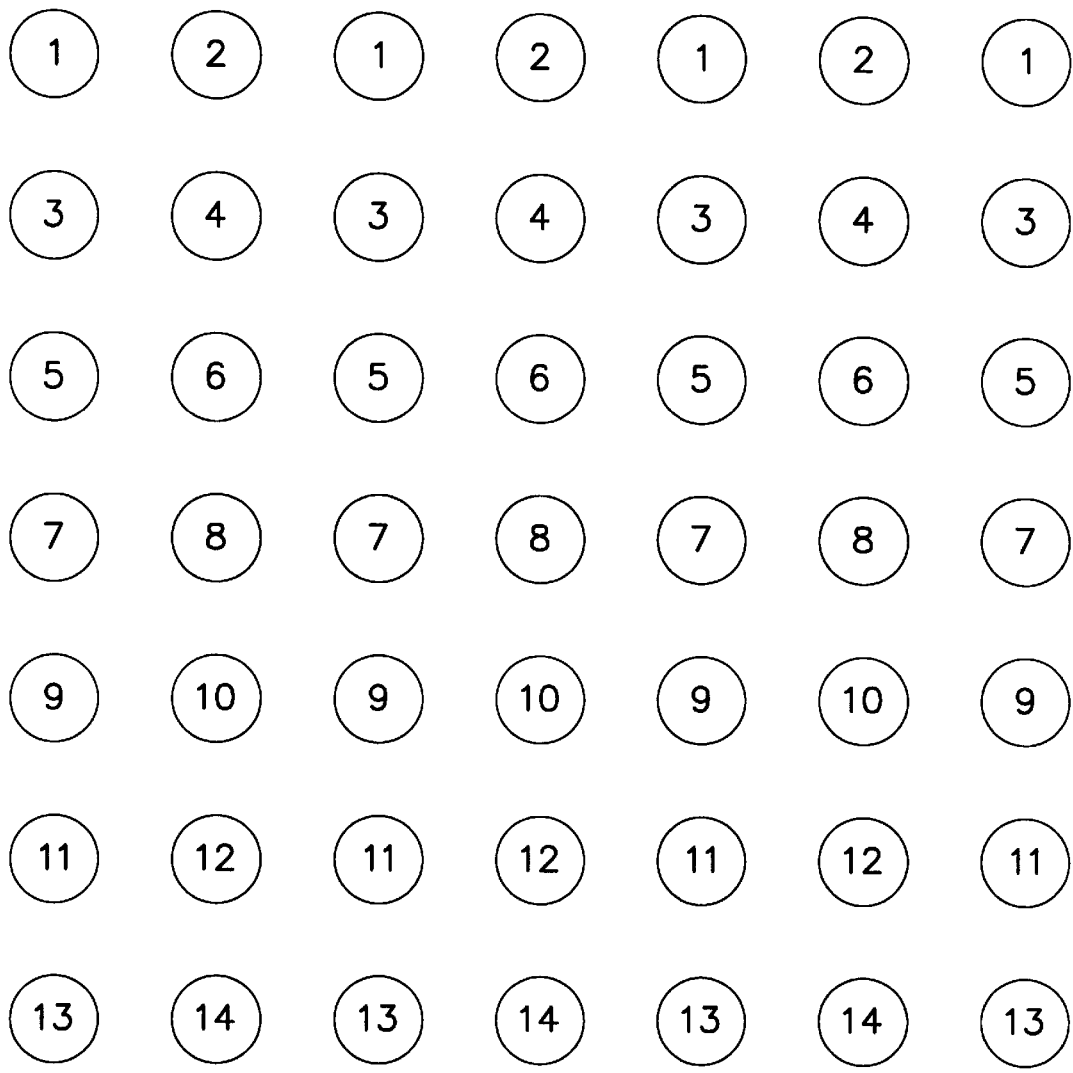
FIG. 13 is a schematic illustration of an alternate electrode connection mode.

Referring to FIG. 13, an array of needles is illustrated wherein all of the needles with the same number are connected in parallel. As can be seen, by switching all needles 1 and 2 against needles 3 and 4, then all needles 1 and 3 against all needles 2 and 4 and then reversing the polarity, only four pulses are needed to cover the entire tissue area between the first row and the second row. The effectiveness of this approach has been verified.

This arrangement can be carried out by a two-layer circuit board which requires only 14 connections to the pulse generator. In the illustrated lay-out, all of the same numbers are connected to the same conductor connection in parallel. This entire array can be made up on a two-layer printed circuit board. The principal of switching zones in parallel can be varied further with so many needles in parallel that only four pulses are needed to switch the entire template of 49 needles.

Figure 14:
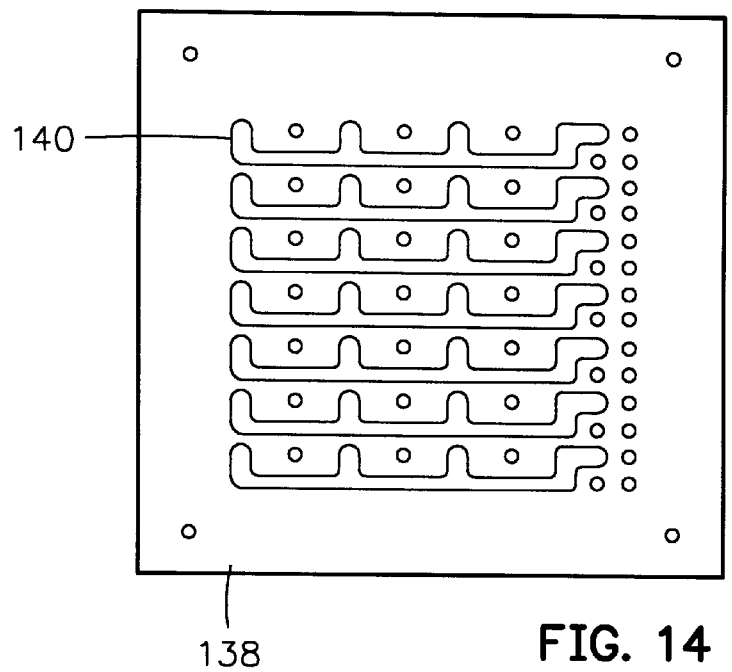
FIG. 14 a plan view of a PC board showing circuit connections for the layout of FIG. 13.
Figure 15:
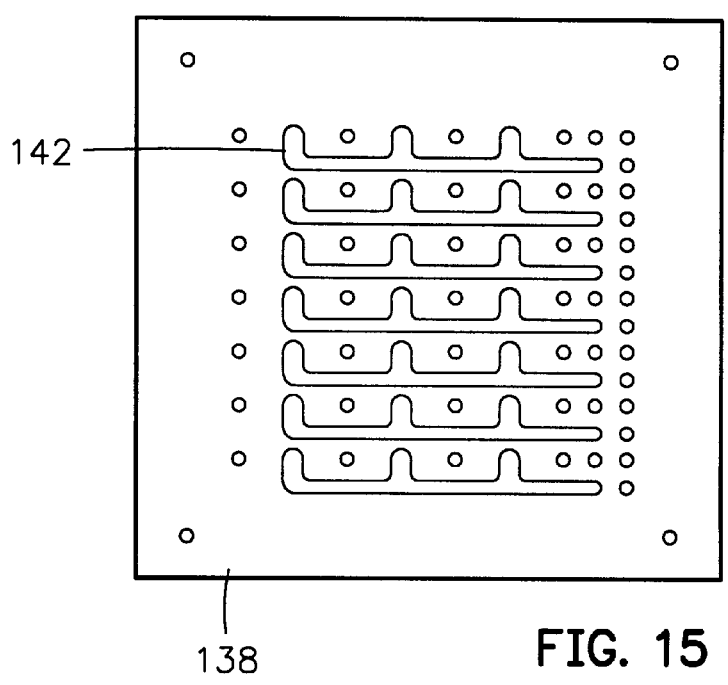
FIG. 15 is a view like FIG. 14 of a second series of connections for the layout of FIG. 13.

Referring to FIGS. 14 and 15, a multi-layer connecting template 138 showing a conductor 140 connecting four of the needle connecting ports in a first row in parallel. A second layer which may be internal or the reverse side of the same board is shown in FIG. 15 with a conductor 142 connecting the three remaining of the needle sockets in the first row in parallel. Thus, with this arrangement, seven conductors on each layer can connect all sockets on the entire board in this manner to the pulse generator. The sockets of the circuit board are provided with spring contacts as previously described, which allow the needle electrodes to make sliding contact and to be extended and retracted. This enables them to be easily applied to a design which allows the needles to be extended from and retractable into a holder.

Figure 18:
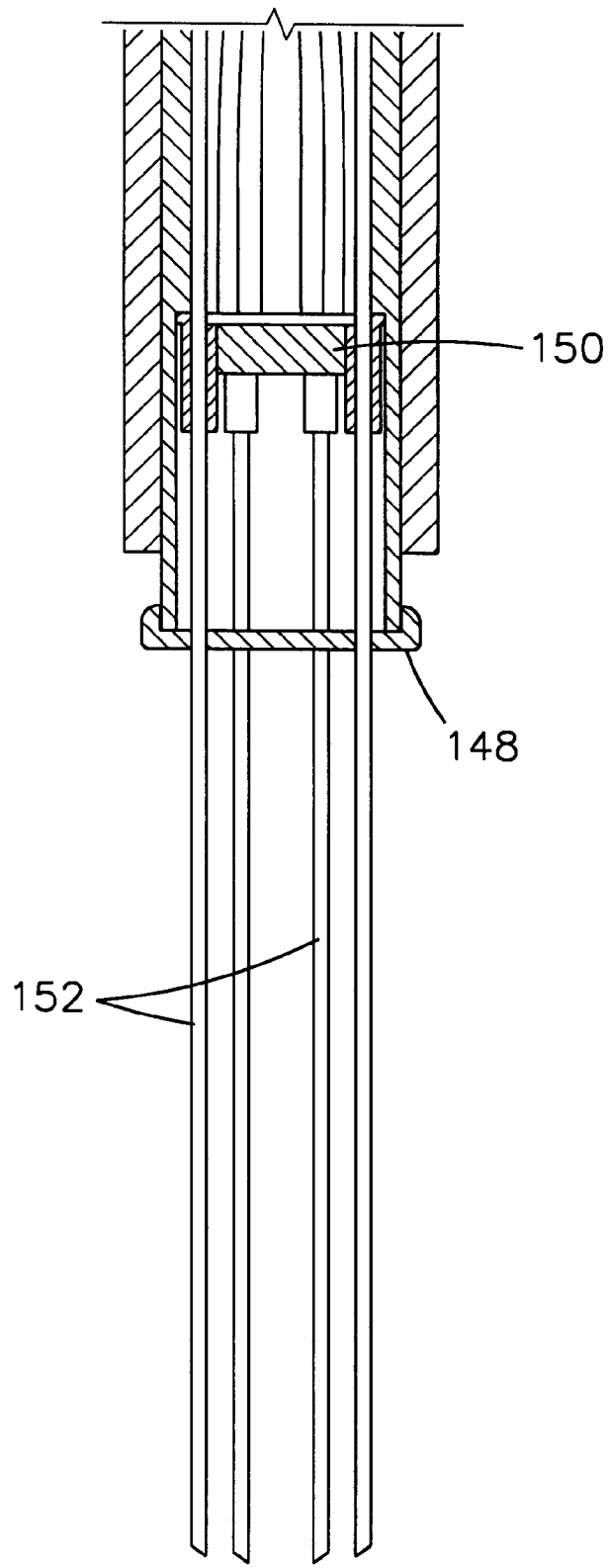
FIG. 18 is an enlarged view showing details of the holder of FIG. 16.

Referring to FIGS. 16–18, an extendable and retractable assembly is illustrated and designated generally by the numeral 144. The assembly comprises an elongated central support member 146 having a head or nose piece 148. A circuit board 150 having a plurality of sliding through-sockets into which needles are mounted on the support member 146 and receive the extending and retracting needles. A plurality of needles 152 are mounted on a tubular sleeve 154 which is mounted on the central support member 146. As the sleeve is moved along the support member, it alternately extends and retracts the needles, as illustrated in FIGS. 16 and 17. The device is also preferably provided with an indicator or gauge 156 to provide an indication of the length of extension of the needles. In operation, the nose piece 148 is placed against the tissue through which the needles are to extend and the sleeve 154 extended until the needle electrodes extend to the desired depth. As in previous embodiments, one or more of the electrodes may be a hollow needle for the introduction of genes or drugs. A cable 158 connects the needle electrodes of the device to a pulse generator.

Figure 19:
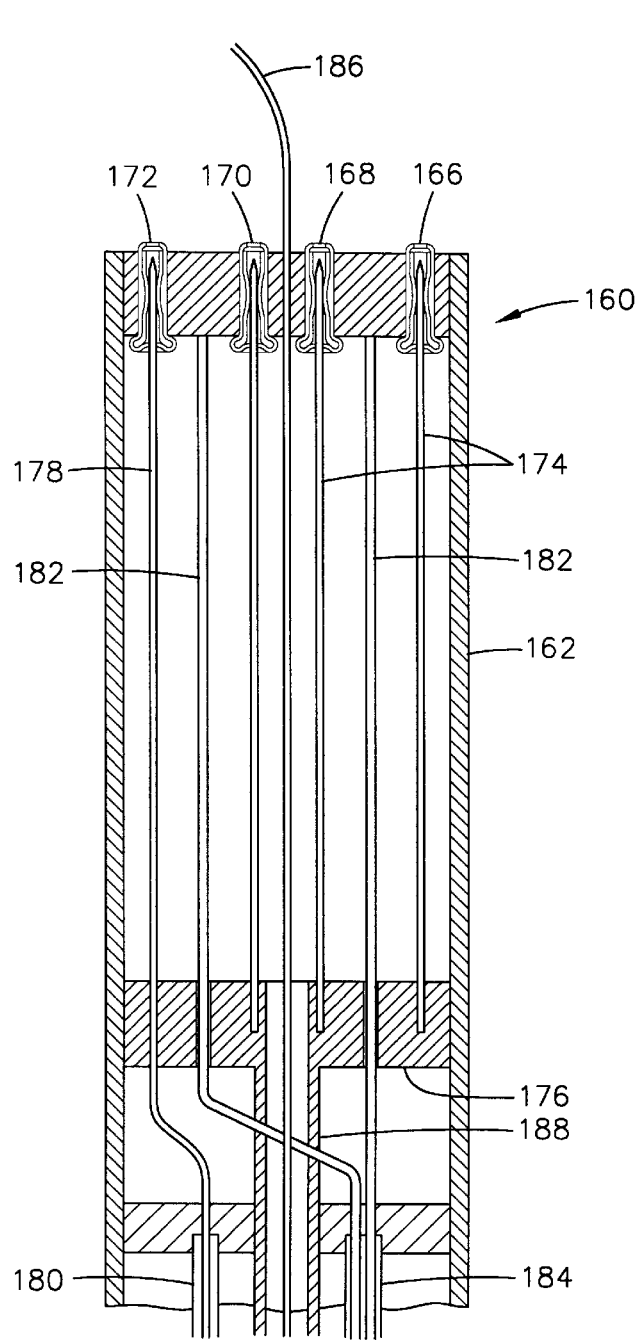
FIG. 19 is a side elevation view in section illustrating an embodiment of the invention like FIG. 16 adapted for a catheter showing the needle electrodes in the retracted position.
Figure 20:
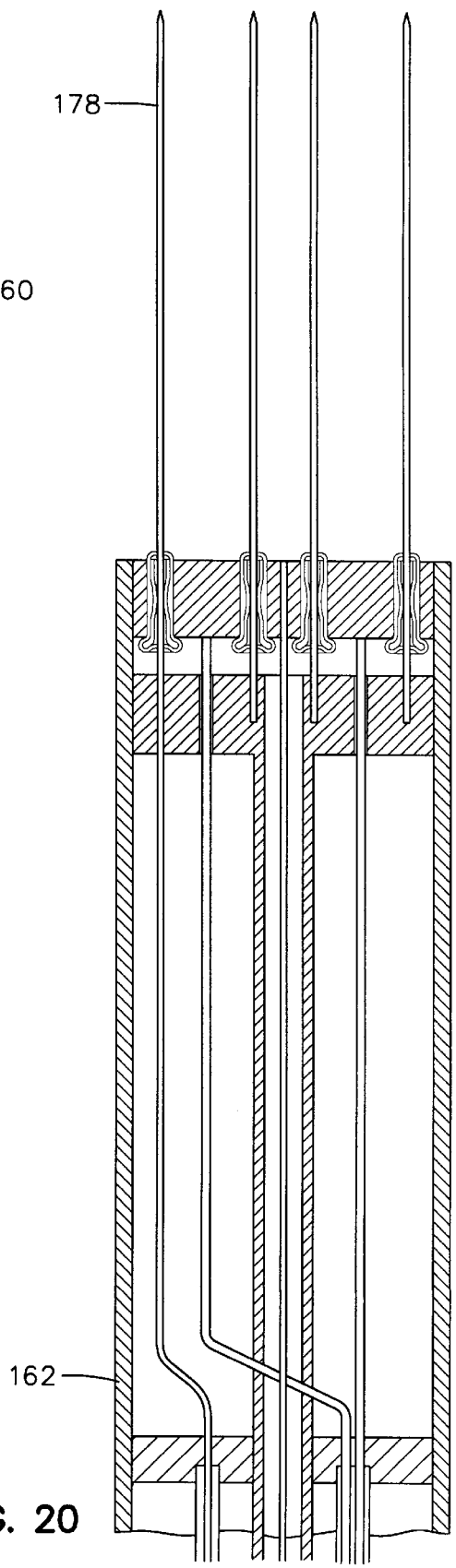
FIG. 20 is a view like FIG. 19 showing the needle electrodes in the extended position.
Figure 21:
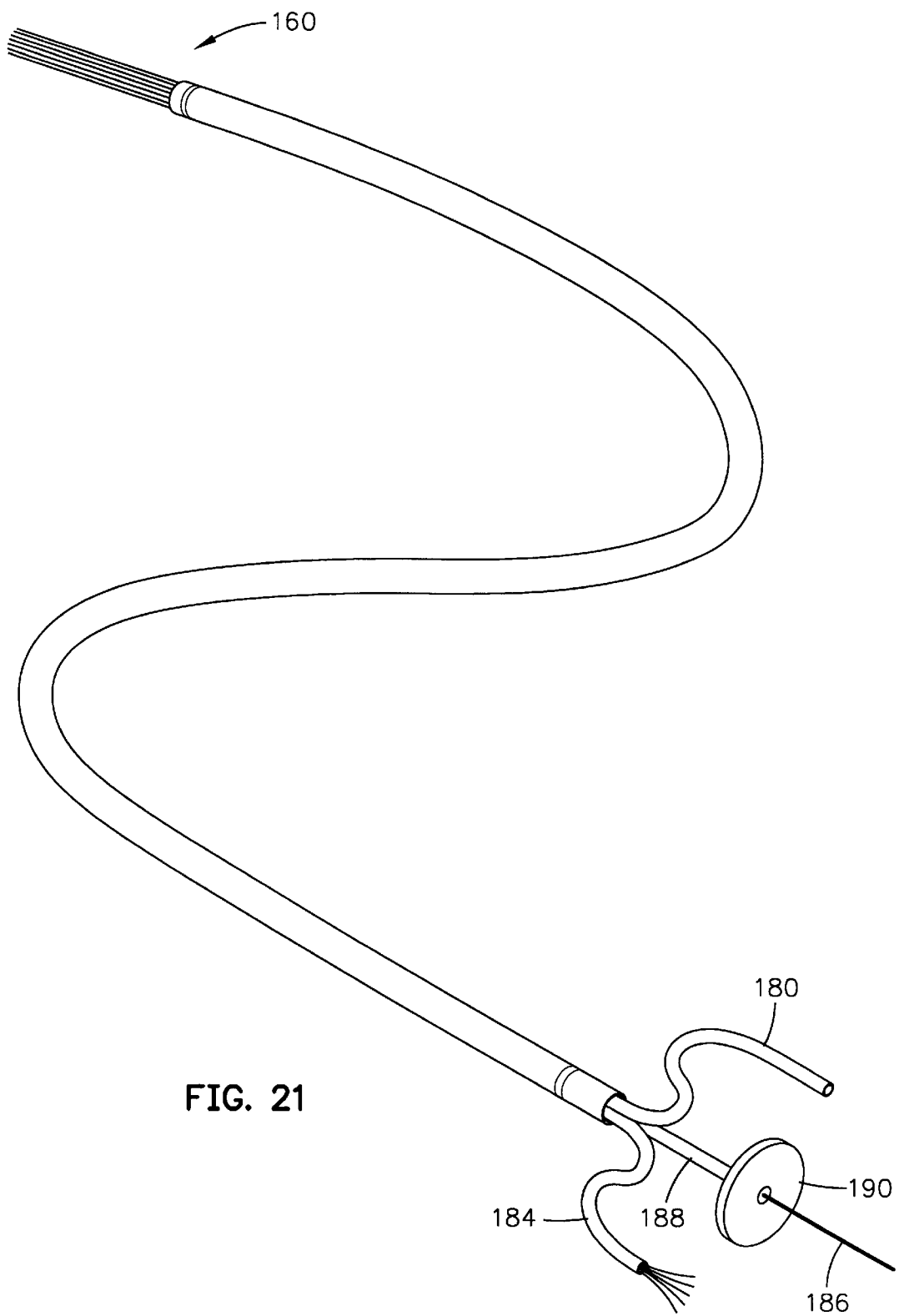
FIG. 21 is a perspective view of a catheter embodying the electrode array of FIG. 19. electrode array of FIG. 16.

The extendable and retractable needles can also be advantageously applied to a catheter. Referring to FIGS. 19–21, a catheter tip assembly is illustrated and designated generally by the numeral 160. In this embodiment, an elongated flexible catheter member 162 is fitted at a distal end with a template 164 having a plurality of through-sockets with sliding connectors 166, 168, 170 and 172. A plurality of solid conductor electrodes 174 are mounted in a moveable actuator plate 176 for movement along the catheter. A hollow needle 178 for the infusion of genes or drugs is mounted in the moveable support plate 176 and extends through one of the through-sockets and by way of a lumen 180 to a source of drugs or genes not shown. As shown in FIG. 20, the needle electrodes may be extended and retracted from the end of the catheter.

As shown in FIG. 21, the catheter is an elongated flexible member having the needles at one end and various connectors and manipulating means at the other end. The infusion lumen 180 extends to the proximal end of the catheter for connection to a source of genes or drugs, as the case may be. A plurality of electrode wires or conductors 182 extend to and through a electrode wire lumen 184. These extend from the end of the lumen 184 at the proximal end of the catheter for connection to a suitable pulse generator. A guide wire 186 extends from the distal end of the catheter and extends the length thereof by way of a lumen 188. The lumen 188 is connected at one end to the moveable support 176 and includes a disk 190 at the proximal end for use in extending and retracting the needles from the end of the catheter.

While I have illustrated and described my invention by means of specific embodiments, it is to be understood that numerous changes and modifications may be made therein without departing from the spirit and scope of the invention, as defined in the appended claims.

I claim:

1. An electrode template apparatus comprising:
   a primary support member comprising a multi-layer printed circuit board having opposite surfaces;
   a plurality of aligned bores through said board and said opposite surfaces; and a plurality of conductors on said support member separately connected to at least one of said plurality of bores
   a plurality of conductors comprising a conductor on each layer connected to a plurality of the bores on the board; and
   means for connecting said conductors to a power supply.

2. An electrode apparatus according to claim 1 wherein said bores are in a rectangular array.

3. An electrode apparatus according to claim 2 wherein said the connections of conductors to electrodes on each board are in a line.

4. An electrode apparatus according to claim 3 wherein said rows are at least three in number.

5. An electrode apparatus according to claim 3 wherein said bores are in multiple rows in a rectangular array.

6. An electrode apparatus according to claim 1 wherein said bores are in a rectangular array, and a plurality of said bores are connected in parallel.

7. An electrode apparatus according to claim 6 wherein said rows are at least three in number.

8. An electrode apparatus according to claim 7 wherein said plurality of electrodes have a needle configuration for insertion into tissue.

9. An electrode apparatus according to claim 8 wherein at least one of said plurality of electrodes have a tubular configuration for injection of molecules into tissue.

10. An electrode apparatus according to claim 1 wherein said plurality of electrodes have a needle configuration for insertion into tissue.

11. An electrode apparatus according to claim 10 wherein at least one of said plurality of electrodes have a tubular configuration for injection of molecules into tissue.

12. An electrode template apparatus comprising:

a primary support member having opposite surfaces;

a plurality of bores extending through said primary support member and through said opposite surfaces;

a plurality of conductors on said support member separately connected to at least one of said plurality of bores;

a moveable support member mounted for movement toward and away from said primary support member;

a plurality of electrodes mounted on said moveable support member and slideably mounted in said plurality of bores so that each conductor is connected to at least one electrode, and so that said plurality of electrodes are extendable and retractable upon movement of said moveable support member toward and away from said primary support member; and means for connecting said conductors to a power supply.

13. An electrode apparatus according to claim 12 wherein one said moveable support member and said primary support member is tubular and the other of said moveable support member and said primary support member is telescopically mounted for movement in said one of said support members.

14. An electrode template apparatus comprising:

a primary support member having opposite surfaces;

a plurality of bores extending through said support member and through said opposite surfaces;

a plurality of conductors on said support member separately connected to at least one of said plurality of bores;

a moveable support member mounted for movement toward and away from said primary support member, one said moveable support member and said primary support member is tubular and the other of said moveable support member and said primary support member is telescopically mounted for movement in said one of said support members, and said support members are disposed on an end of a catheter;

a plurality of electrodes mounted on said moveable support member and slideably mounted in said plurality of bores so that each conductor is connected to at least one electrode; and means for connecting said conductors to a power supply.

15. A needle electrode template apparatus, comprising:

a primary support member having opposite parallel surfaces;

a plurality of bores arranged in a rectangular array and extending through said support member and through said opposite surfaces for slidably mounting and guiding a plurality of needle electrodes into penetrating engagement with tissue;

a plurality of conductors on said support member separately connected to at least one of said plurality of bores;

a plurality of needle electrodes slidably mounted in said plurality of bores so that each conductor is connected to at least one electrode and the electrode is slidably guided into selected penetrating depth of engagement into tissue;

at least one of said needle electrodes having a tubular configuration for injection of molecules into issue and means for connecting said conductors to a power supply.

16. An electrode apparatus according to claim 15 wherein said bores are in rows of at least three in number.

17. An electrode apparatus according to claim 15 wherein:

a moveable support member is mounted for movement toward and away from said primary support member; and said plurality of said needle electrodes are mounted on and moveable with said moveable support member to a selected depth of tissue penetration.

18. An electrode template apparatus, comprising:

a primary support member having opposite parallel surfaces;

a plurality of bores arranged in a rectangular array and extending through said support member and through said opposite surfaces;

a plurality of conductors on said support member separately connected to at least one of said plurality of bores;

a moveable support member mounted for movement toward and away from said primary support member, wherein one said moveable support member and said primary support member is tubular and the other of said moveable support member and said primary support member is telescopically mounted for movement in said one of said support members;

a plurality of electrodes mounted on said moveable support member and slideably mounted in said plurality of bores so that each conductor is connected to at least one electrode;

at least one of said needle electrodes having a tubular configuration for injection of molecules into issue and means for connecting said conductors to a power supply, wherein one said moveable support member and said primary support member is tubular and the other of said moveable support member and said primary support member is telescopically mounted for movement in said one of said support members.

19. An electrode apparatus according to claim 18 wherein said support members are disposed on an end of a catheter.

20. An electrode template apparatus, comprising:

a primary support member comprising multiple printed circuit boards having opposite surfaces;

a plurality of aligned bores through said boards and through said opposite surfaces;

a conductor on each board separately connected to at least one of said plurality of the bores on each board;

a plurality of electrodes selectively insertable in said plurality of bores so that each conductor is connected to at least one electrode; and means for connecting said conductors to a power supply.

21. An electrode template apparatus, comprising:

a primary support member having opposite surfaces;

a plurality of elongated guide bores extending through said support member and through said opposite surfaces for receiving and guiding needle electrodes into selected depths of penetrating engagement with tissue;

a plurality of conductors on said support member separately connected to at least one of said plurality of bores;

a plurality of elongated needle electrodes adapted to be selectively mounted in said plurality of guide bores so that each conductor is connected to at least one electrode and the electrode is extendable and retractable from said support while guided into selected penetrating depth of engagement into tissue; and means for connecting said conductors to a power supply.

22. An electrode apparatus according to claim 21 wherein said bores include a tubular conductive member having spring biased contacts are in rows of at least three in number.

23. An electrode apparatus according to claim 21 wherein said bores are in rows of at least three in number.

* * * * *